(12) United States Patent
Kinney

(10) Patent No.: US 7,477,376 B2
(45) Date of Patent: Jan. 13, 2009

(54) SELF-CALIBRATING OPTICAL REFLECTANCE PROBE SYSTEM

(75) Inventor: Terrance R. Kinney, South Bend, IN (US)

(73) Assignee: Control Development Incorporated, South Bend, IN (US)

( * ) Notice: Subject to any disclaimer, the term of this patent is extended or adjusted under 35 U.S.C. 154(b) by 0 days.

(21) Appl. No.: 11/770,180

(22) Filed: Jun. 28, 2007

(65) Prior Publication Data

US 2008/0013085 A1 Jan. 17, 2008

Related U.S. Application Data

(62) Division of application No. 10/711,129, filed on Aug. 26, 2004.

(60) Provisional application No. 60/481,485, filed on Oct. 8, 2003.

(51) Int. Cl.
*G01N 21/01* (2006.01)

(52) U.S. Cl. ...................................... 356/244

(58) Field of Classification Search ................. 356/244, 356/300, 303, 445
See application file for complete search history.

(56) References Cited

U.S. PATENT DOCUMENTS

| | | | | |
|---|---|---|---|---|
| 3,935,463 | A * | 1/1976 | Jacobsen | 250/373 |
| 4,577,110 | A * | 3/1986 | MacBride et al. | 250/461.2 |
| 5,974,210 | A * | 10/1999 | Alcock et al. | 385/31 |
| 2008/0013085 | A1* | 1/2008 | Kinney | 356/244 |

* cited by examiner

*Primary Examiner*—Roy M Punnoose
(74) *Attorney, Agent, or Firm*—Hartman & Hartman, P.C.; Gary M. Hartman; Domenica N.S. Hartman

(57) ABSTRACT

A self-calibrating optical reflectance probe system having an illuminant light source to illuminate a sample material, optical pickup means to collect reflected light from the sample material, and an articulated white reference reflection standard for illuminant reference to provide a system capable of accurately measuring optical reflectance and automated verification of proper operation. The probe system preferably employs an uncomplicated mount using a single pipe fitting and clamp.

12 Claims, 3 Drawing Sheets

SELF-CALIBRATING OPTICAL REFLECTANCE PROBE SYSTEM

This is a division patent application of co-pending U.S. patent application Ser. No. 10/711,129, filed Aug. 26, 2004, which claims the benefit of U.S. Provisional Application No. 60/481,485, filed Oct. 8, 2003.

BACKGROUND OF THE INVENTION

The invention relates to an optical reflectance probe system for the illumination of a sample material and detection of reflected light.

Optical reflectance measurements are commonly used for the analysis of materials. In a typical optical reflectance system, light is shown upon the material to be analyzed. An optical detector/measurement instrument gathers some of the light reflected off of the material and measures the intensity of the light either at specific wavelengths or across a spectral range yielding a measurement of intensity versus wavelength.

Materials can be analyzed in this way for the presence of certain constituents, the amount of these constituents, and the uniformity of these constituents throughout the consignment of the material. Specific uses include measurement of blend uniformity in pharmaceutical products, water or other solvent content in pharmaceutical products, measurement of protein, carbohydrates and water in agricultural products, and the presence of foreign material in an otherwise homogeneous material such as flour. Other applications include paint matching, quality control for paper, textiles, packaging, food, pharmaceuticals and cosmetics.

Typically, an arrangement of a light source, lenses and mirrors are used to align and project the illumination from the light source through a viewport window onto the sample material. Then additional lenses and mirrors are used to capture the light reflected from the sample material and guide it to the optical detector/measurement instrument. Optical fibers are also commonly used to guide the illumination light to the sample and/or optical pickup fibers to capture and guide the reflected light from the sample material back to the optical detector/measurement instrument. Common light sources include incandescent and particularly tungsten-halogen lamps. Common optical detector/measurement instruments include photometers, monochronometers and optical spectrographs.

Optical reflectance measurement systems require calibration. Calibration includes the use of reflectance standards including white references, references with known spectral signatures, spectral line sources, transmissive filters, and shutters. Calibration generally takes place during manufacture of the optical detector/measurement instrument, and commonly again after the system components are integrated. Calibration of the system can change due to vibration, temperature change or other conditions, so it is common to recalibrate periodically to ensure the system is performing within a required accuracy. In certain applications, such as the production of pharmaceutical products, there are government regulations requiring periodic verification of performance, and again, requiring the use of these calibration standards.

Current optical reflectance measurement systems require that some or all of these standards be employed by an operator dismounting the probe and manually introducing these references for the system to sample. This can be a cumbersome and time consuming task, as the system may be mounted at a point generally inaccessible. The unit could easily be damaged during the removal, or during reinstallation, requiring the system to be repaired, recalibrated, or worse, go unnoticed where data generated by the system is relied upon to produce safe and effective product.

In process control or quality control applications, optical reflectance measurement systems are required to be adjacent to the sample material being measured. Where the sample material is contained in a chamber, such as a vacuum chamber, mixer, blender or environmental chamber, the optical reflectance probe must view the sample material through a viewport window. This window must withstand pressures, abrasion, chemical attack, and provide a seal between the probe and the chamber interior, while providing a clear optical path for the probe to view. Further, mounts for the optical reflectance measurement system must be provided to hold the probe in reference to the window to view the sample material within the chamber.

Current window and mount systems employ a flat viewport window and a series of mounting brackets. The viewport window reflects some of the illuminant light from the probe back into the probes collecting optics, thus distorting the reflectance measurement. Anti-reflection coatings on the window reduce but do not eliminate this back reflection. Further, these coatings cannot be applied to the inner surface of the window because some of the coating may abrade off, contaminating the material, and generally cannot withstand chemical attack and other environmental conditions. Other means to reduce effects caused by this back reflection require complicated optical schemes including collimation and focusing optics. The mounting brackets are generally custom for the particular chamber and optical reflectance probe being employed, and must be designed special for each application. Further, due to constraints placed by chamber geometry and the requirements of bracket position and orientation to the window, placement of the window at a desired viewing position may not be possible for certain applications.

BRIEF SUMMARY OF THE INVENTION

The present invention provides a self-calibrating optical reflectance probe system having an illuminant light source to illuminate a sample material, optical pickup means to collect reflected light from the sample material, and an articulated white reference reflection standard for illuminant reference. The probe system preferably has multiple illuminant light sources for redundancy and multiple optical pickup fibers for diversity in reflected light detection for more accurate measurements. Additional optional but preferred elements for the probe system include an optical line source for wavelength calibration and verification, a spectral reference standard for dynamic range verification and/or wavelength calibration and verification, a transmissive filter for dynamic range measurement and a shutter for dark reference, a curved window to reduce reflected light from the window surface, and an uncomplicated mount preferably employing a single sanitary pipe fitting and clamp (both preferably common to industry), which serves as the viewport as well and the probe mount, eliminating the need for additional brackets to mount the optical reflectance probe assembly. An additional fixture employing an integral curved window can be welded onto a chamber containing the material to be detected, thus providing a seal between the chamber and the probe assembly and simultaneously providing the required mount for the probe assembly. These components can be used individually or severally to calibrate the optical reflectance probe system and verify proper and accurate operation without the removal of the system from its installation, and all by automation without the intervention of an operator. The components, including the reference standards, are preferably enclosed within the assembly so as to be sealed from contamination and protected from damage due to handling.

It is therefore an object of the invention to provide an optical reflectance probe system incorporating means that enables the system to self-calibrate and verify calibration without operator intervention.

It is another object of the invention to provide an optical reflectance probe system with a viewport window that reduces back reflection.

Yet another object of the invention is to provide an optical reflectance probe system with an uncomplicated mount using components common to industry, eliminating the need for custom mounting brackets.

Still another object of the invention is to provide an optical reflectance probe system having a viewport incorporated within a probe mount to eliminate the need for additional mounting brackets.

The above and other objects, features and advantages of the invention will be apparent from the following description taken in connection with the accompanying drawings.

BRIEF DESCRIPTION OF THE DRAWINGS

These and other objects and purposes of the invention will be best understood in view of the following detailed description of the invention taken in conjunction with the appended drawings, wherein.

DESCRIPTION OF THE INVENTION

Figure 1:
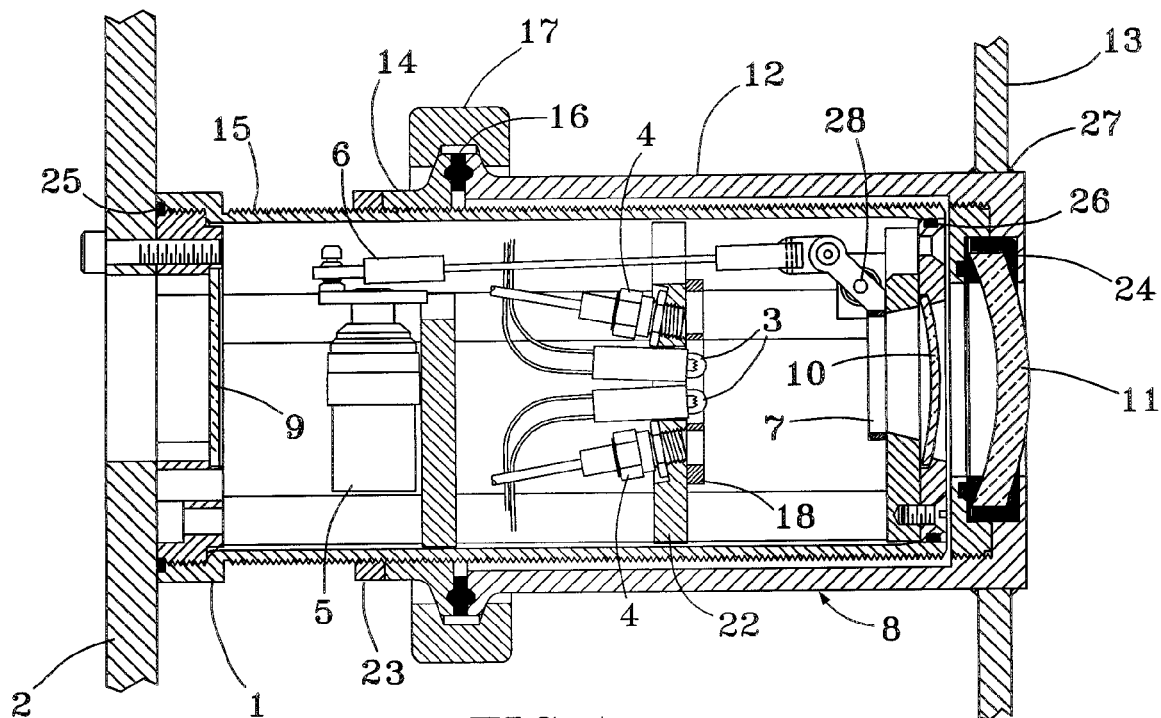
FIG. 1 schematically shows a cross-sectional view of a self-calibrating optical reflectance probe system and mount with a reference standard positioned in a referencing position.

Referring to FIG. 1, a self-calibrating optical reflectance probe system in accordance with a preferred embodiment of the invention is shown as including a probe housing 1 that encases components of an optical reflectance probe, and a probe mount 8 for mounting the housing 1 to a chamber 13 where a material (not shown) is to be sampled. Seals 25 and 26 prevent contaminants from entering the probe housing 1. The probe housing 1 has a threaded exterior 15, allowing a pipe fitting flange 14 of the probe mount 8 to be adjusted along the length of the probe housing 1 to position the end of the probe system at a desired distance from a viewport window 11 within the probe mount 8. A locking ring 23 is shown as preventing the pipe fitting flange 14 from moving in relation to the probe housing 1. The locking ring 23 cooperates with the flange 14, a clamp 17, and a gasket 16 to hold the optical reflectance probe on a sanitary pipe fitting 12. The sanitary pipe fitting 12 is mounted by a weld 27 in a hole cut in the chamber 13. The sanitary pipe fitting 12 houses the viewport window 11, which is sealed against egress of the sample material by a seal 24. The seal 24 can be made of an inert material such as Teflon® so as to not contaminate any material in the chamber 13. The viewport window 11 is preferably made of sapphire for abrasion resistance as well as chemical resistance, again so as not to contaminate the sample material in the chamber 13. Within the probe system there are two sample illumination lamps 3 and four optical pickup fibers 4 (two of which can be seen in FIG. 1) uniformly dispersed for diversity in sensing the reflected light from the sample material. A white reference standard 7 is provided in the form of a disk of diffuse reflective material, such as Spectralon®. This white reference standard 7 is mounted on an articulating mount rotatable on a bearing 28 and driven by a linkage 6 and actuator 5. In FIG. 1, the white reference standard 7 is shown in the "white reference" position, i.e., in an optical path through the probe system. Further, a shutter/filter wheel 18 is shown attached to an optic mounting plate 22. An electronic control module 9 controls all of activities of the lamps 3 and actuator 5 via communications from an optical detector/measurement instrument (not shown) of any suitable type. The back of the probe system can be mounted to either a breakout box for communication and powering the probe system as well as interconnecting to the optical pickup fibers 4, or directly to the optical detector/measurement instrument. FIG. 1 shows a mounting end 2 of a breakout box or detector/measurement instrument attached with screws to the probe housing 1, such that the mount 8 is the singular mount for the probe system, or optionally a combination of the probe system and optical detector/measurement instrument.

Figure 2:
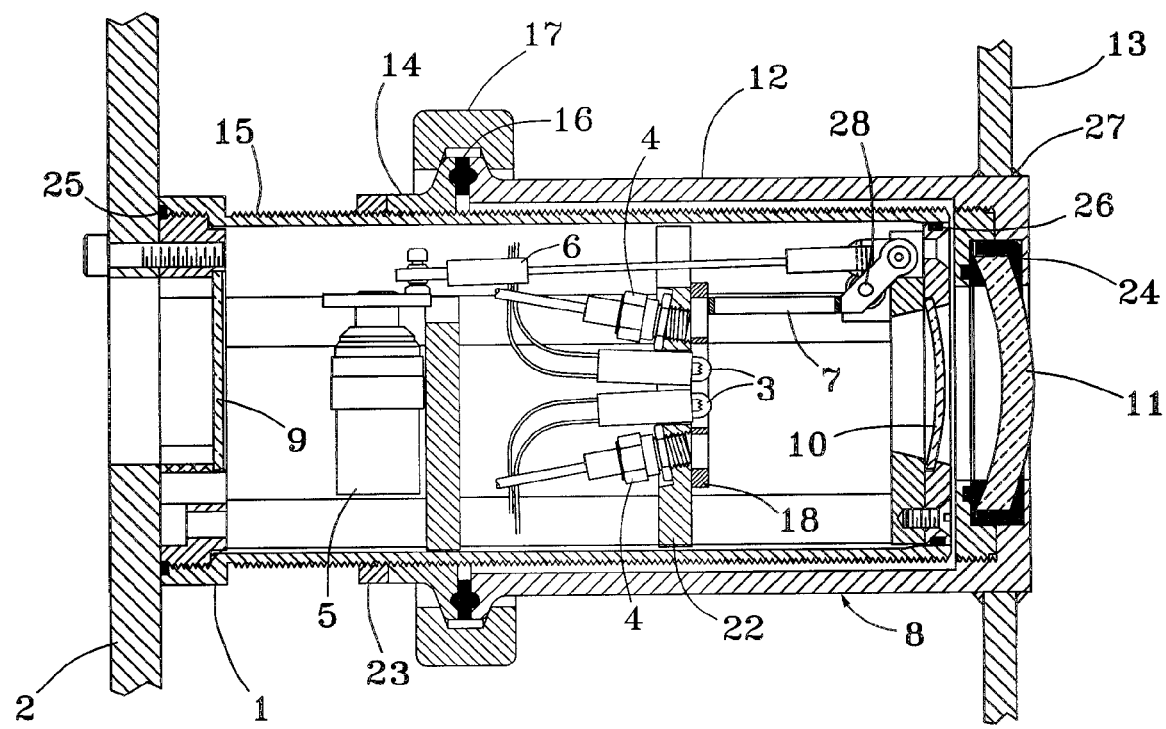
FIG. 2 is similar to FIG. 1 but shows the probe system and mount with the reference standard positioned out of an optical path of the probe system.

In FIG. 2, the probe system is shown in a material sampling mode with the white reference standard 7 rotated into a position out of the optical path of the probe system, such that light generated by the sample illumination lamps 3 is reflected back to the optical pickup filters 4.

Figure 3:
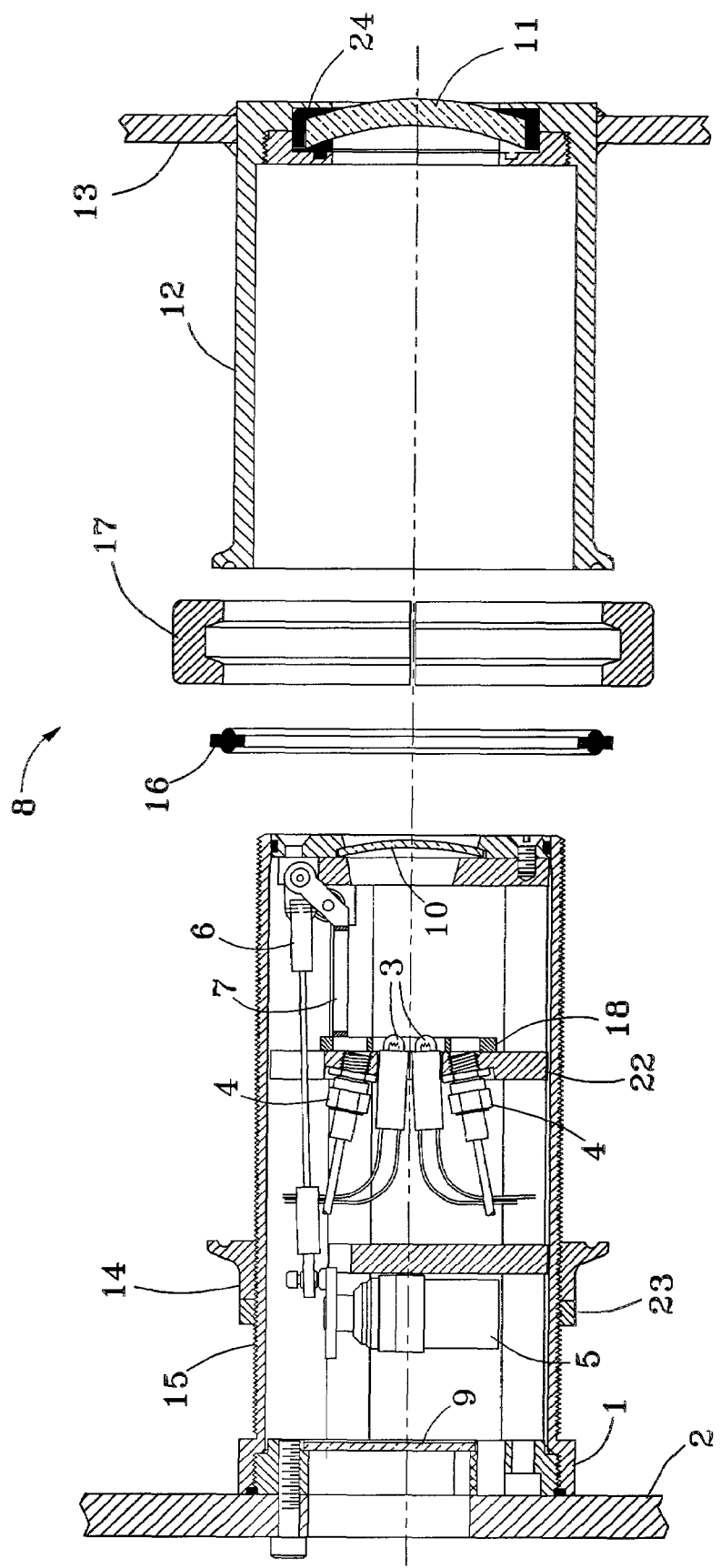
FIG. 3 schematically shows a cross-sectional view of the probe system and mount of FIG. 1 with the probe system and mount separated to depict individual components used for mounting.

FIG. 3 shows the gasket 16, clamp 17, and sanitary pipe fitting 12 of the probe mount 8 separated from the probe housing 1 to more readily show how the probe system is mounted.

Figure 4:
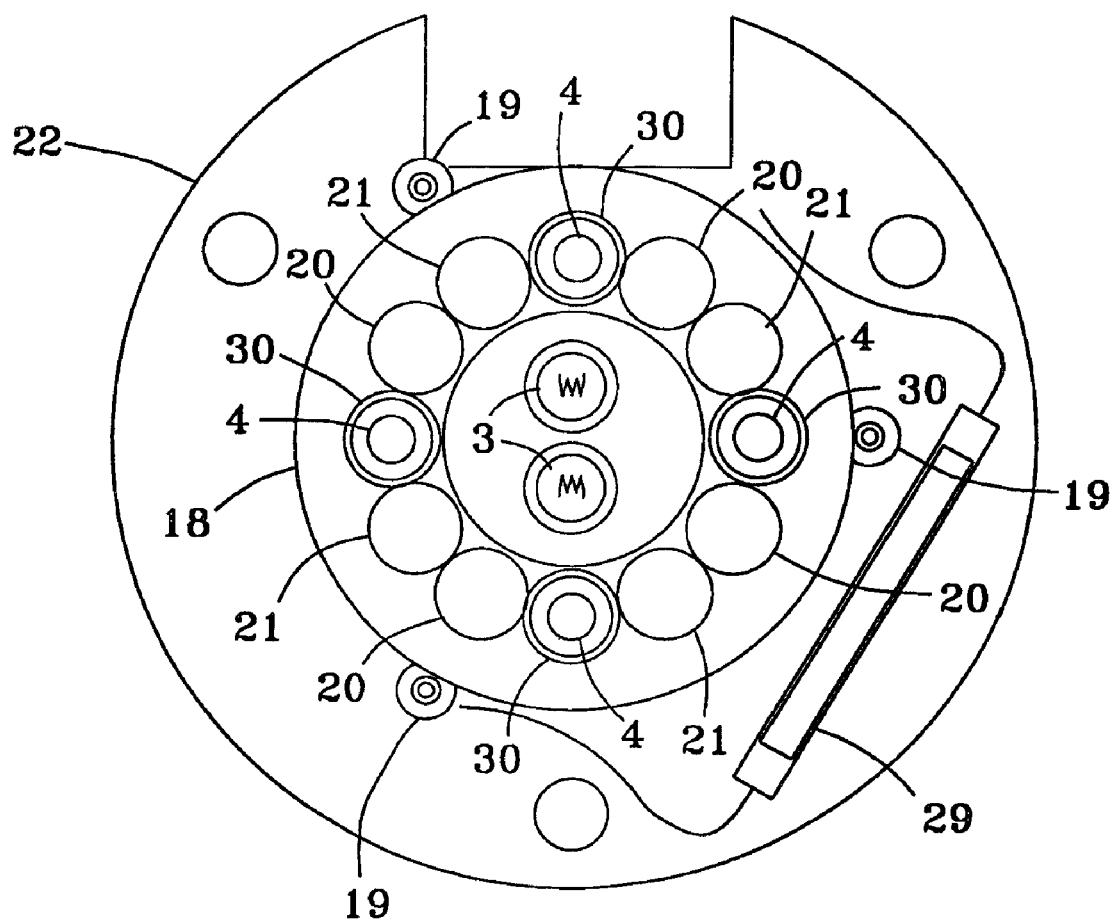
FIG. 4 shows an isolated end view of a transmissive filter and shutter components and a spectral line source of the probe system of FIG. 1 in relation to optical pickup fibers and an illuminant light source of the probe system.

FIG. 4 depicts an end on view of the optic mounting plate 22, showing a preferred arrangement for the sample illumination lamps 3, optical pickup fibers 4, and shutter/filter wheel 18, the latter of which is mounted for rotation on bearings 19 and driven by an actuator (not shown). FIG. 4 further depicts individual shutters 20, open apertures 30, and individual transmissive filters 21. Also, the mounting position for a spectral line source 29 is shown.

Operation of the probe system will be described in reference to the Figures. During operation, only one of the illumination lamps 3 need be powered (the other being provided for redundancy) to illuminate the white reference standard 7 (FIG. 1), whose diffuse reflectance of the illuminant is partially captured by the optical pickup fibers 4. The light captured by the optical pickup fibers 4 is processed and used as a high level (white) reference signal. The white reference standard 7 remains in this position, preventing light passing through the window 11 from reaching the pickup fibers 4. The illumination lamp 3 is then turned off or the pickup fibers 4 are shuttered by rotating the shutter/filter wheel 18 to position the shutters 20 over the pickup fibers 4. A dark signal captured by the pickup fibers 4 at this time is processed and used as a low level (dark) reference signal.

Further testing of the system can be administered by rotating the shutter/filter wheel 18, positioning the transmissive filters 21 over the optical pickup fibers 4, again with the white reference standard 7 deployed and the illumination lamp 3 powered. Depending on the filter chosen for the transmissive filters 21, stray light can be measurement or spectral accuracy verified. If a time-integrating optical detector/measurement instrument (such as a photo detector array based spectrograph) is employed, system linearity can be measured by deploying the white reference standard 7 and the illumination lamp 3 powered and the shutter/filter wheel 18 positioning the open apertures 30 over the optical pickup fibers 4, then sampling the captured light at varying integration times set in the optical detector/measurement instrument. Spectral resolution and accuracy can be measured by deploying the white reference standard 7 while the illumination lamp 3 is de-powered, the shutter/filter wheel 18 positions the open apertures 30 over the optical pickup fibers 4, and the spectral line source 29 is powered. Light from the spectral line source 29 will reflect off the white reference standard 7 and a potion thereof is subsequently captured by the optical pickup fibers 4. The light captured by the optical pickup fibers 4 can be processed yielding both spectral accuracy and spectral resolution.

During material sampling, the white reference standard 7 is retracted as shown in FIG. 2, the illumination lamp 3 powered, and the shutter/filter wheel 18 positioned such that the open apertures 30 are over the optical pickup fibers 4. Light from the illumination lamp 3 passes through a dust window 10 and again through the viewport window 11 onto the sample material within the chamber 13. The dust window 10 and viewport window 11 have curvatures such that their inner and outer curvatures are spherical and their inner and outer center of curvatures are substantially at the same locus point. Further, the center of curvatures of the dust and viewport windows 10 and 11 are positioned substantially at the level of the lamps 3 and on center with the probe system. This arrangement maintains minimal effect on the light passing through the windows 10 and 11, while all light reflected from the lamp 3 by the surfaces of the windows 10 and 11 is to a great degree projected back to the lamps 3 and away from the optical pickup fibers 4. This arrangement also provides greater structural strength for the viewport window 11, allowing for higher loads or a thinner window 11 for an existing load specification. Additionally, the curved shape allows sample material to more easily fall away from the window 11, and enables sample material to be blown clean from the window 11 with an air jet to a greater degree than a flat window would allow. Light passing through both windows 10 and 11 and reaching the sample material is reflected back through the windows 10 and 11, where some of the reflected light is captured by the optical pickup fibers 4. This light is then processed by the optical detector/measurement instrument and, with information gained from the white reference and dark reference signals, yields information about the sample material itself.

If in operation, the lamp 3 being used fails, the second lamp 3 can be powered and a new white reference signal generated using the process outlined above to again ready the system for material sampling. This switching of lamps 3 and all testing described above can be automated and performed without operator intervention. Documentation on test results required by regulatory agencies can also be automatically generated, again without operator intervention. In systems employing more than one probe system, each probe system can have the capability of determining itself unhealthy and report this to the system gathering data, which would then take appropriate action, such as calling service for the probe system that declared itself unhealthy and not using data gathered from the unhealthy probe system.

In a variation of this system, a second reference standard could be installed with a second actuator to employ a reference standard with a known spectral signature. In operation of this embodiment, the white reference standard 7 would be retracted, the second reference standard deployed, the illumination lamp 3 powered and the shutter/filter wheel 18 positioned such that the open apertures 30 are over the optical pickup fibers 4. Light captured by the optical pickup fibers 4 is then analyzed for spectral signature, both wavelength accuracy and absorption level accuracy.

While the invention has been described in terms of specific embodiments, it is apparent that other forms could be adopted by one skilled in the art. For example, the probe system and its components could differ in appearance and construction from the embodiments shown in the Figures, and appropriate materials could be substituted for those noted. Accordingly, it should be understood that the invention is not limited to the specific embodiments illustrated in the Figures. It should also be understood that the phraseology and terminology employed above are for the purpose of disclosing the illustrated embodiments, and do not necessarily serve as limitations to the scope of the invention. Therefore, the scope of the invention is to be limited only by the following claims.

The invention claimed is:

1. A mount for an optical reflectance probe having a probe housing with an exterior surface, the mount comprising a pipe fitting and means for securing the probe housing to the pipe fitting, the pipe fitting having an opening at a first end thereof, the pipe fitting being sized to receive a portion of the probe housing therein through the opening thereof, the securing means being disposed at the first end of the pipe fitting and configured to secure the probe housing to the pipe fitting by engaging the exterior surface of the probe housing while the portion of the probe housing is within the pipe fitting.

2. The mount according to claim 1, wherein the mount further comprises an integral viewport window at one end of the pipe fitting.

3. The mount according to claim 2, wherein the viewport window comprises a curved surface to reduce reflected light from the window.

4. The mount according to claim 1, wherein the engaging means is threadably engageable with the exterior surface of the probe housing.

5. The mount according to claim 4, wherein the securing means comprises a pipe fitting flange threadably engageable with the exterior surface of the probe housing, and a clamp for securing the pipe fitting flange to the pipe fitting.

6. The mount according to claim 5, wherein the securing means further comprises a gasket secured by the clamp between the pipe fitting flange and the pipe fitting.

7. The mount according to claim 1, wherein the mount is part of a system that comprises the optical reflectance probe.

8. The mount according to claim 7, wherein the optical reflectance probe is assembled with the mount and the portion of the probe housing is within the pipe fitting.

9. A mount for an optical reflectance probe having a probe housing with a threaded exterior surface, the mount comprising:

a sanitary pipe fitting sized to contain an end portion of the probe housing and having an integral curved viewport window to reduce reflected light from the window surface; and a clamping assembly coupled with the sanitary pipe fitting for mounting the end portion of the probe housing within the sanitary pipe fitting, the assembly comprising a pipe fitting flange threadably engageable with the threaded exterior surface of the probe housing, and a clamp for securing the pipe fitting flange to the sanitary pipe fitting.

10. The mount according to claim 9, wherein the clamping assembly further comprises a gasket secured by the clamp between the pipe fitting flange and the sanitary pipe fitting.

11. The mount according to claim 9, wherein the mount is part of a system that comprises the optical reflectance probe.

12. The mount according to claim 11, wherein the optical reflectance probe is assembled with the mount and the end portion of the probe housing is within the sanitary pipe fitting.

* * * * *